United States Patent [19]

Kodama et al.

[11] Patent Number: 4,472,386
[45] Date of Patent: Sep. 18, 1984

[54] 5-FLUORO-(β-URIDINE OR 2'-DEOXY-β-URIDINE) DERIVATIVES, A PROCESS FOR PRODUCING THE SAME AND A CARCINOSTATIC AGENT CONTAINING THE SAME

[75] Inventors: Tsutomu Kodama; Masaakira Senoura; Hajime Aoyama; Tomonobu Yamaguchi; Isao Kitayama; Minako Yotsuji; Toru Hiraiwa; Masaharu Omori; Nobuo Terashima; Yutaka Kodama, all of Toyama, Japan

[73] Assignee: Toyama Chemical Co., Ltd., Tokyo, Japan

[21] Appl. No.: 46,109

[22] Filed: Jun. 6, 1979

[30] Foreign Application Priority Data

Jun. 10, 1978 [JP] Japan ................................. 53-69383

[51] Int. Cl.$^3$ ...................... A61K 31/70; C07H 19/06; C07H 19/08
[52] U.S. Cl. ........................................ 424/180; 536/23
[58] Field of Search ........................... 536/23; 424/180

[56] References Cited

U.S. PATENT DOCUMENTS 3,309,359 3/1967 Dreschensky et al. ................ 536/23
3,975,367 8/1976 Gish et al. ............................. 536/23

OTHER PUBLICATIONS

Heidelberger, C. et al., Biochim. Biophys. Acta., vol. 76, 312–314, 1963.
Khwaja, T. et al., J. Of Medicinal Chemistry, vol. 13, 64–69, 1970.
Heidelberger, C. et al., Proc. Soc. Exper. Biol. & Med., vol. 97, 470–475, 1958.

Primary Examiner—Blondel Hazel
Attorney, Agent, or Firm—Griffin, Branigan & Butler

[57] ABSTRACT

5-Fluoro-(β-uridine or 2'-deoxy-β-uridine) derivatives having an acyl group at the 3-position of the molecule. These compounds are useful as carcinostatic agent. This disclosure relates to such compounds, a process for producing the same and a carcinostatic agent comprising such a compound.

12 Claims, No Drawings

5-FLUORO-(β-URIDINE OR 2'-DEOXY-β-URIDINE) DERIVATIVES, A PROCESS FOR PRODUCING THE SAME AND A CARCINOSTATIC AGENT CONTAINING THE SAME

This invention relates to a novel 5-fluoro-(β-uridine or 2'-deoxy-β-uridine) derivative, a process for producing the same, and a carcinostatic agent comprising the same.

Carcinostatic substances which have hitherto been commercially available have problems in both carcinostatic activity and toxicity. Particularly, they induce, after administration, various symptoms such as a depression of leukocyte count, a depression of thrombocyte count, epilation, suppression of bone marrow, nausea and vomiting, diarrhea, and the like, which is considered as a problem in clinical treatments.

On the other hand, 5-fluoro-2'-deoxy-β-uridine, commonly called FUDR, is already known to exhibit an intense carcinostatic activity in vitro and have a low toxicity (C. Heidelberger et al., Proc. Soc. Exp. Biol. Med., 97, 470 (1958)).

In vivo, however, it lacks persistency (in other words, it is excreted rapidly) and it is readily decomposed by nucleotide-phosphorylase to yield 5-fluorouracil (G. D. Birnie, Biochem. Biophys. Acta., 76, 315 (1963)) so that the above-mentioned properties which the time-dependent metabolic antagonist FUDR originally has cannot be exhibited.

Under such circumstances, the present inventors have conducted earnest studies with the aim of providing a compound having an intense carcinostatic activity, a low toxicity and other excellent properties by increasing its protein-binding ability, preventing the decomposition in a living body and increasing its persistency. As a result, it has been found that the above-mentioned object can be realized by a compound represented by the general formula (I), which appear hereinafter.

It is an object of this invention to provide a novel 5-fluoro-(β-uridine or 2'-deoxy-β-uridine) derivative having an acyl group at the 3-position of the molecule.

It is another object of this invention to provide a novel 5-fluoro-(β-uridine or 2'-deoxy-β-uridine) derivative having an intense carcinostatic activity and a low toxicity.

It is yet another object of this invention to provide a carcinostatic agent comprising a novel 5-fluoro-(β-uridine or 2'-deoxy-β-uridine) derivative as its active ingredient.

It is still another object of this invention to provide a process for producing a novel 5-fluoro-(β-uridine or 2'-deoxy-β-uridine) derivative.

Other objects and advantages of this invention will be apparent from the following description.

According to this invention, there is provided a 5-fluoro-(β-uridine or 2'-deoxy-β-uridine) derivatives represented by the general formula (I):

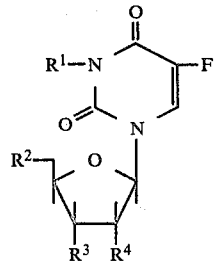

wherein $R^1$ represents acyl; $R^2$ and $R^3$, which may be identical or different, represent protected or unprotected hydroxyl; and $R^4$ represents hydrogen or protected or unprotected hydroxyl, as well as to a process for producing the same and a carcinostatic agent comprising the same.

In the compounds of this invention represented by the general formula (I), $R^1$ represents acyl. Specific examples of said acyl include aroyl, such as benzoyl, 3,4-methylenedioxybenzoyl, naphthoyl and the like; $C_{1-18}$ alkanoyl, such as acetyl, propionyl, butyryl, valeryl, isobutyryl, isovaleryl, pivaloyl, palmitoyl, stearoyl and the like; heterocyclic carbonyl (this heterocyclic ring contains 1 to 4 hetero atoms selected from O, S and N), such as thenoyl, furoyl, thiazolylcarbonyl, oxazolylcarbonyl, isoxazolylcarbonyl, nicotinoyl and the like; and $C_{3-5}$ alkenoyl such as acryloyl, crotonoyl and the like. All these acyl groups may have one or more substituents selected from halogens, such as fluorine, chlorine, bromine, or iodine; hydroxyl; nitro; cyano; amino; carboxyl; $C_{1-12}$ acyl, such as formyl, acetyl, propionyl, butyryl, acryloyl, crotonoyl, benzoyl, naphthoyl, furoyl, thenoyl and the like; halogen-substituted derivatives of said acyl; $C_{1-12}$ acyloxy, such as acetyloxy, propionyloxy, butyryloxy, acryloyloxy, benzoyloxy, naphthoyloxy, furoyloxy, thenoyloxy and the like; halogen-substituted derivatives of said acyloxy; $C_{1-5}$ alkylamino such as methylamino, ethylamino, butylamino and the like; halogen-substituted derivatives of said alkylamino; di-$C_{1-5}$ alkylamino, such as dimethylamino, diethylamino, dibutylamino, methylethylamino and the like; halogen-substituted derivatives of said dialkylamino; $C_{1-12}$ acylamino, such as acetylamino, propionylamino and the like; halogen-substituted derivatives of said acylamino; $C_{1-5}$ alkyl, such as methyl, ethyl, propyl, butyl and the like; halogen-substituted derivatives of said alkyl; $C_{1-10}$ alkoxy such as methoxy, ethoxy, propoxy, butoxy, pentoxy, octyloxy and the like; halogen-substituted derivatives of said alkoxy; $C_{1-5}$ alkoxycarbonyl, such as methoxycarbonyl, ethoxycarbonyl, propoxycarbonyl, butoxycarbonyl and the like; halogen-substituted derivatives of said alkoxycarbonyl; aryl such as phenyl, naphthyl and the like; halogen-substituted derivatives of said aryl; heterocyclic groups (this heterocyclic ring contains 1 to 4 hetero atoms selected from O, S and N), such as furyl, thienyl and the like and their halogen-substituted derivatives; and the like. As the protecting group in the protected hydroxyl groups represented by $R^2$, $R^3$ and $R^4$, there may be employed those groups which are conventionally used for the protection of hydroxyl group. Examples of said protecting group include $C_{1-10}$ alkanoyl, such as acetyl, propionyl, isopropionyl, butyryl, isobutyryl, sec-butyryl, tert-butyryl and the like; $C_{1-10}$ alkoxycarbonyl, such as methoxycarbonyl, ethoxycarbonyl, propoxycarbonyl, isopropoxycarbonyl and the like; $C_{1-12}$ acyloxy-$C_{1-12}$ acyl, such as acetyloxymethylcarbonyl, propionyloxymethylcarbonyl, acetyloxyethylcarbonyl, α-(acetyloxy)-propionyl, β-(propionyloxy)-propionyl and the like; substituted aroyl, such as p-chlorobenzoyl, p-methylbenzoyl, p-nitrobenzoyl, m,p-dinitrobenzoyl and the like; and mono-, di- and tri-halogeno-$C_{1-10}$ alkanoyl, such as chloroacetyl, dichloroacetyl, trichloroacetyl, fluoroacetyl, difluoroacetyl, trifluoroacetyl, bromoacetyl, dibromoacetyl, tribromoacetyl, iodoacetyl, diiodoacetyl, triiodoacetyl and the like.

Among the above-mentioned compounds of this invention, preferable is a compound in which $R^1$ is benzoyl substituted by fluorine or chloroacetylamino, or 3,4-methylenedioxybenzoyl.

The compound of this invention can be produced by reacting a compound represented by the general formula (II):

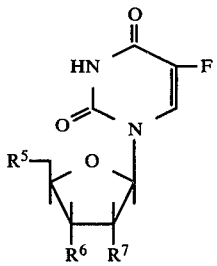

(II)

wherein $R^5$ and $R^6$ represent protected hydroxyl and $R^7$ represents hydrogen or protected hydroxyl with a reactive derivative of a compound represented by the general formula (III):

(III)

wherein $R^1$ is as defined above, in the presence or absence of a base, and then optionally subjecting the reaction product to alcoholysis to remove the protecting group from the protected hydroxyl group. In the general formula (II), the protecting groups of the protected hydroxyl groups represented by $R^5$, $R^6$ and $R^7$ may be the same as those of $R^2$, $R^3$ and $R^4$ in the general formula (I). In order to selectively eliminate only the protecting group from the protected hydroxyl group after the reaction between the compound represented by the general formula (II) and the reactive derivative of the compound represented by the general formula (III), it is preferable to use an active protecting group having an electronegative group. Specific examples of said active protecting group include substituted benzoyl, such as p-nitrobenzoyl, m,p-dinitrobenzoyl and the like; mono-, di- or tri-halogenoalkanoyl such as chloroacetyl, dichloroacetyl, trichloroacetyl, fluoroacetyl, difluoroacetyl, trifluoroacetyl, bromoacetyl, dibromoacetyl, tribromoacetyl, iodoacetyl, diiodoacetyl, triiodoacetyl and the like; trialkylsilyl such as trimethylsilyl and the like; and 1,3,2-dioxaphospholanyl such as 4-methyl-1,3,2-dioxaphospholanyl and the like.

In the general formula (III), $R^1$ represents the same acyl group as mentioned above. Examples of said reactive derivative include acid halides, acid azides, acid cyanides, mixed acid anhydrides, active esters, active acid amides and the like. Depending on the kind of the reactive derivative used, an inorganic or organic base such as an alkali hydroxide, an alkali carbonate, an alkali acetate, triethylamine, trimethylamine, tributylamine, pyridine, N-methylmorpholine or the like may be added. It is particularly preferable to use an acid halide such as acid chloride, acid bromide or the like in combination with triethylamine.

Specifically, the compound of this invention can be produced as follows:

A compound represented by the general formula (II) is dissolved or suspended in a solvent inert to the reaction, such as acetone, tetrahydrofuran, dioxane, acetonitrile, dimethylformamide, diethyl ether, diisopropyl ether, benzene, toluene, dichloroethane, methylene chloride, chloroform, ethyl acetate, methyl ethyl ketone or the like or a mixture of two or more, and reacted with a reactive derivative of the compound represented by the general formula (III) at a temperature of −50° C. to +100° C., preferably at room tempeature or an elevated temperature, in the presence or absence of the base. The reaction is usually effected for 5 minutes to 24 hours. In eliminating the protecting group from the protected hydroxyl group after completion of the reaction, alcoholysis is carried out by use of an alcohol such as methanol, ethanol, propanol, isopropanol or the like in the presence of a base or an acid as a catalyst. The said base includes organic bases such as trimethylamine, tirethylamine, tributylamine, pyridine, N-methylmorpholine or the like. The said acid includes organic and inorganic acids such as hydrogen chloride, sulfuric acid, phosphoric acid, formic acid, trifluoroacetic acid, trichloroacetic acid, p-toluene sulfuric acid and the like. When acyl is used as the protecting group, it is preferred to carry out the alcoholysis with methanol in the presence of triethylamine as the catalyst. When trialkylsilyl or 1,3,2-dioxaphospholanyl is used, it is preferred to carry out the alcoholysis with methanol in the presence of hydrogen chloride as the catalyst. This alcoholysis may be carried out either in succession to the above-mentioned reaction or after the product has been isolated. It is carried out in the above-mentioned solvent or a mixture of two or more of said solvents, or an alcohol.

The alcoholysis is usually carried out for 5 minutes to 12 hours, after which the objective compound is isolated by a conventional way, for example, a chemical means for separation and purification such as solvent-extraction and the like.

The carcinostatic effect and acute toxicity of the typical compounds of this invention are as follows:

1. Experiment on the inhibition of Ehrlich solid tumor
   (a) Experimental procedure Ehrlich ascites carcinoma was subcutaneously inoculated into the right inguinal region of ddY mice (5 weeks old, male, 8 mice per group) with $3 \times 10^6$ cells per mouse.

24 Hours after the inoculation, a test drug suspended or dissolved in 5% HCO 60 (a product manufactured by Nikkol) was administered intraperitoneally successively once daily for 7 days. To the control group, the same quantity as above of 5% HCO 60 was intraperitoneally administered in the same manner. Fourteen days after the inoculation, the tumor was excised and weighed, from which the average tumor weight ratio between the test group and the control group (T/C) was determined.

TABLE 1

[Structure: uracil with R¹-N, F, attached to deoxyribose sugar with HO, OH groups]

| | Compound* | Dose (mg/kg) | Body weight change (g) | No. of surviving mice/No. of total mice used | T/C (%) |
|---|---|---|---|---|---|
| Positive control | FUDR | 40 | +6.5 | 8/8 | 47.1 |
| | 5-Fu | 20 | +4.1 | " | 49.9 |
| Compound No. | | | | | |
| 1 | ClCH₂COONH—⌬(OCH₃)—CO— | 40 | −0.8 | 8/8 | 19.4 |
| 2 | F—⌬—CO— | " | +6.8 | " | 23.2 |
| 3 | ⌬(F)—CO— | " | +5.4 | " | 24.2 |
| 4 | ClCH₂CONH—⌬—CO— | " | +4.4 | " | 25.2 |
| 5 | ClCH₂CONH—⌬—CO— | " | +4.8 | " | 27.5 |
| 6 | ⌬(CH₃)—CO— | " | +7.3 | " | 32.3 |
| 7 | ⌬(Cl)—CO— | " | +6.0 | " | 33.1 |
| 8 | ⌬(I)—CO— | " | +7.6 | " | 33.5 |

TABLE 1-continued

[Structure: R¹-N substituted pyrimidine with fluorine, attached to a sugar moiety with HO and OH groups]

| Compound* | | Dose (mg/kg) | Body weight change (g) | No. of surviving mice/No. of total mice used | T/C (%) |
|---|---|---|---|---|---|
| 9 | [1-naphthyl]-CO— | " | +6.7 | " | 33.5 |
| 10 | [phenyl with OCH₃, NH₂, Cl substituents]-CO— | " | +7.3 | " | 34.2 |
| 11 | [3-chlorophenyl]-CO— | " | +7.6 | " | 34.3 |
| 12 | $CH_3OCO$-[phenyl]-CO— | " | +6.2 | " | 36.9 |
| 13 | NC-[phenyl]-CO— | " | +7.2 | " | 36.9 |
| 14 | OHC-[phenyl]-CO— | " | +7.1 | " | 38.1 |
| 15 | [furan-2-yl]-CO— | " | +7.9 | " | 39.1 |
| 16 | [3-methyl-thiophen-2-yl]-CO— | " | +6.4 | " | 40.7 |
| 17 | [3,5-dihydroxyphenyl]-CO— | " | +7.9 | " | 41.0 |

TABLE 1-continued

[Structure: R¹-N-containing pyrimidine with F substituent, attached to a deoxyribose with HO and OH groups]

| Compound* | | Dose (mg/kg) | Body weight change (g) | No. of surviving mice/No. of total mice used | T/C (%) |
|---|---|---|---|---|---|
| 18 | 2,6-(OCH₃)₂-C₆H₃-CO— | " | +7.8 | " | 41.5 |
| 19 | 4-O₂N-C₆H₄-CO— | " | +5.9 | " | 41.5 |
| 20 | 2-F-C₆H₄-CO— | " | +7.4 | " | 42.8 |
| 21 | 4-(CH₃)₂N-C₆H₄-CO— | " | +4.7 | " | 32.4 |
| 22 | 4-Cl₂CHCONH-C₆H₄-CO— | " | +6.5 | " | 41.6 |
| 23 | 4-Br-thiophene-2-CO— | " | +5.3 | " | 38.8 |
| 24 | 5-Br-furan-2-CO— | " | +4.7 | " | 42.5 |
| 25 | 3-F₃C-C₆H₄-CO— | " | +5.3 | " | 43.0 |
| 26 | 4-BrCH₂CONH-C₆H₄-CO— | " | +2.3 | " | 35.3 |

TABLE 1-continued

[Structure: R¹—N with pyrimidine ring containing F, attached to sugar with HO, OH groups]

| Compound* | Dose (mg/kg) | Body weight change (g) | No. of surviving mice/No. of total mice used | T/C (%) |
|---|---|---|---|---|
| 27 [methylenedioxybenzoyl—CO—] | " | +6.4 | " | 27.1 |
| 28 [difluorobenzoyl (F,F)—CO—] | " | +5.9 | " | 21.7 |
| 29 [difluorobenzoyl (F,F ortho)—CO—] | " | +7.9 | " | 41.3 |
| 30 [methylenedioxybenzoyl—CO—] (3',5'-di-O—acetyl compound) | " | +6.1 | " | 30.1 |

Note:
*In the case of the compounds of this invention, only $R_1$ of the above-mentioned formula is specified.

(b) Experimental procedure

Ehrlich ascites carcinoma was subcutaneously inoculated into the inguinal region of ddY mice (5 weeks old, male, 8 mice per group) with $3 \times 10^6$ cells per mouse. Six days after the inoculation, a test drug dissolved or suspended in 0.5% CMC solution was administered orally to the test group successively once daily for 10 days, while the same quantity as above of 0.5% CMC solution was orally administered to the control group. Twenty one days after the inoculation, the tumor was excised and weighed, from which the average tumor weight ratio between the test group and the control group (T/C) was determined.

TABLE 2

| Compound (No.) | Dose (mg/kg) | Body weight change (g) | No. of surviving mice/No. of total mice used | T/C (%) |
|---|---|---|---|---|
| FUDR | 60 | −2.7 | 8/8 | 48.6 |
| 5-Fu | 30 | −3.8 | " | 39.7 |
| 2 | 60 | −0.4 | " | 36.8 |
| 5 | 60 | −4.1 | " | 34.0 |
| 27 | 60 | −0.5 | " | 30 |

TABLE 2-continued

| Compound (No.) | Dose (mg/kg) | Body weight change (g) | No. of surviving mice/No. of total mice used | T/C (%) |
|---|---|---|---|---|
| 0.5% CMC | — | +1.2 | 10/10 | — |

2. Experiment on the inhibition of Sarcoma-180 ascites tumor (a) Experimental procedure Sarcoma-180 ascites tumor was subcutaneously inoculated into the right inguinal region of ddY mice (5 weeks old, male, 8 mice per group) with $3 \times 10^6$ cells per mouse. Twenty four hours after the inoculation, a test drug dissolved in 10% polyethylene glycol was administered intravenously to the test group successively once daily for 7 days, while the same quantity as above of 10% polyethylene glycol was intravenously administered to the control group. Ten days after the inoculation, the tumor was excised and weighed, from which the average tumor weight ratio between the test group and the control group (T/C) was determined.

TABLE 3

| Compound (No.) | Dose (mg/kg) | Body weight change (g) | No. of surviving mice/No. of total mice used | T/C (%) |
| --- | --- | --- | --- | --- |
| FODR | 10 | +3.9 | 8/8 | 56.3 |
| 5-Fu | 5 | +4.0 | 8/8 | 59.7 |
| 2 | 10 | +4.1 | 8/8 | 46.2 |
| 27 | 10 | +4.0 | 8/8 | 45.3 |

3. Acute toxicity test (a) The test compound was suspended in 0.25% CMC solution and administered intraperitoneally to SLC-ddY mice (5 weeks old, male, 6 mice per group). The number of dead mice was counted over the subsequent three weeks. As a result, no dead mice were observed in the cases of compounds No. 2, 11, 13, 18 and 27 at a dose of 1,000 mg/kg.

(b) The test compound was suspended in 0.25% CMC solution and administered orally to SLC-ddY mice (5 weeks old, male, 6 mice per group). The number of dead mice was counted over the subsequent 3 weeks. $LD_{50}$ value was calculated according to the method of Van der Waerden.

TABLE 4

| Compound (No.) | $LD_{50}$ (mg/kg) |
| --- | --- |
| FUDR | 1328 |
| 5-Fu | 259 |
| 2 | 2073 |
| 21 | ≧2540 |
| 27 | ≧2289 |

4. Carcinostatic test

Experimental procedure

Ehrlich ascites carcinoma was subcutaneously inoculated into the right inguinal region of ddY mice (5 weeks old, male, 8 mice per group) with $8 \times 10^6$ cells per mouse. Twenty four hours after the inoculation, 5, 10, 20 or 40 mg/kg of a test drug suspended or dissolved in polyethylene glycol was administered orally to the test group successively once daily for 10 days, while the same quantity as above of 10% polyethylene glycol was administered orally to the control group. Fourteen days after the inoculation, the tumor was excised and weighed, from which the average tumor weight ratio between the test group and the control group (T/C) was calculated. ED value was determined by the least square method.

TABLE 5

| Compound (No.) | $ED_{40}$ (mg/kg) | $ED_{30}$ (mg/kg) |
| --- | --- | --- |
| FUDR | 24 | 19 |
| 5-Fu | 25 | 15 |
| 2 | 20 | 11 |
| 27 | 12 | 6.4 |

From Tables 1, 3 and 5, it is understandable that the compounds of this invention have an excellent carcinostatic activity and exhibit their efficacy at a low dose. From Table 2, it is understandable that the compounds of this invention are effective even against tumors which are in an advanced stage of growth. The results of acute toxicity tests (a) and (b) demonstrate that the compounds of this invention have much lower toxicity as compared with the control agents.

Carcinostatic agents containing the compounds of this invention, i.e. 5-fluoro-(β-uridine or 2'-deoxy-β-uridine) derivatives, may be formulated in the usual way into conventional preparation forms such as tablet, capsule, syrup, injection or drip and may be administered either orally or non-orally. The dose is generally 0.1-300 mg/kg per day in 1 to 6 portions, though the dose and the number of repetitions of administration may be appropriately varied.

By way of the following examples, the process for producing the compounds of this invention will be explained.

EXAMPLE 1

(a) At room temperature, 1.15 ml of triethylamine was dropped into a mixture of 3 g of 3',5'-di-O-chloroacetyl-5-fluoro-2'-deoxy-β-uridine, 1.15 ml of p-chlorobenzoyl chloride and 7.5 ml of anhydrous methylene chloride with stirring. The resulting mixture was subjected to reaction at room temperature for about 5 hours and thereafter washed with 20 ml of water, 20 ml saturated aqueous solution of sodium bicarbonate and 20 ml of water in this order. The organic layer was dried over anhydrous sodium sulfate and the solvent is distilled off under reduced pressure. The residue was purified by silica gel column chromatography (eluent:-chloroform) to obtain 3.4 g (yield 95%) of amorphous 3-p-chlorobenzoyl-3',5'-di-O-chloroacetyl-5-fluoro-2'-deoxy-β-uridine.

IR (KBr) cm$^{-1}$: $\nu_{C=O}$ 1780, 1750(sh), 1715, 1670.

(b) In 10 ml of tetrahydrofuran was dissolved 3.4 g of the 3-p-chlorobenzoyl-3',5'-di-O-chloroacetyl-5-fluoro-2'-deoxy-β-uridine obtained in (a), to which 10 ml of methanol was added. While stirring the mixture at room temperature, 0.5 ml of triethylamine was added and the reaction was effected for about one hour. The reaction mixture was concentrated under reduced pressure and purified by silica gel column chromatography (eluent: a 20:1 mixture of chloroform and methanol). The eluate was concentrated under reduced pressure, and a small quantity of ethyl acetate was added to the concentrate. Thus, there was obtained 1.7 g (yield 94%) of crystalline 3-p-chlorobenzoyl-5-fluoro-2'-deoxy-β-uridine having a melting point of 152°-155° C.

IR (KBr) cm$^{-1}$: $\nu_{C=O}$ 1740, 1705, 1650

UV (ethanol) nm: $\lambda_{max}$ 261

Rf value: 0.70 (developing solvent: ethyl acetate:formic acid:water=65:5:5)

EXAMPLE 2

(a) At room temperature, 1.15 ml of triethylamine was added to a mixture of 3 g of 3',5'-di-O-chloroacetyl-5-fluoro-2'-deoxy-β-uridine, 1.73 g of p-fluorobenzoyl chloride and 7.5 ml of anhydrous methylene chloride with stirring. The resulting mixture was subjected to reaction at room temperature for about 4 hours and thereafter treated in the same manner as in Example 1(a). Thus, there was obtained 4.1 g (yield 98%) of amorphous 3-p-fluorobenzoyl-3',5'-di-O-chloroacetyl-5-fluoro-2'-deoxy-β-uridine having a decomposition point of 225°-235° C.

IR (KBr) cm$^{-1}$: $\nu_{C=O}$ 1735, 1705, 1660

UV (ethanol) nm: $\lambda_{max}$ 256

Rf value: 0.68 (developing solvent: n-hexane:benzene:ethyl acetate=1:1:2)

(b) 4.1 g of the 3-p-fluorobenzoyl-3',5'-di-O-chloroacetyl-5-fluoro-2'-deoxy-β-uridine obtained in (a) was dissolved in a solvent mixture of 10 ml of tetrahydrofuran and 10 ml of methanol. To the resulting mixture was added 0.5 ml of triethylamine, and the reaction was effected at room temperature for 4 hours. Thereafter, the reaction mixture was treated in the same manner as in Example 1(b). Thus, there was obtained 2.38 g (yield 88%) of 3-p-fluorobenzoyl-5-fluoro-2'-deoxy-β-uridine in the form of white crystals having a melting point of 130°–133° C.

IR (KBr) cm$^{-1}$: $\nu_{C=O}$ 1745, 1705, 1660(sh), 1640

UV (ethanol) nm: $\lambda_{max}$ 208, 255

Rf value: 0.73 (developing solvent: ethyl acetate:formic acid:water=65:5:5)

EXAMPLE 3

(a) At room temperature, 1.15 ml of triethylamine was dropped into a mixture of 3 g of 3',5'-di-O-chloroacetyl-5-fluoro-2'-deoxy-β-uridine, 2.1 g of p-chloroacetylaminobenzoyl chloride and 7.5 ml of anhydrous methylene chloride with stirring, and the resulting mixture was subjected to reaction for about 4 hours. Then the solvent was distilled off under reduced pressure, and the residue was dissolved in ethyl acetate and treated in the same manner as in Example 1(a). Thus, there was obtained 3.95 g (yield 90%) of crystalline 3-p-chloroacetylaminobenzoyl-3',5'-di-O-chloroacetyl-5-fluoro-2'-deoxy-β-uridine having a melting point of 183°–184° C.

IR (KBr) cm$^{-1}$: $\nu_{C=O}$ 1740, 1710, 1660

UV (ethanol) nm: $\lambda_{max}$ 300

Rf value: 0.43 (developing solvent: n-hexane:benzene:ethyl acetate=1:1:2)

(b) In a mixed solvent of 10 ml of tetrahydrofuran and 10 ml of methanol was dissolved 3.95 g of the 3-p-chloroacetylaminobenzoyl-3',5'-di-O-chloroacetyl-5-fluoro-2-deoxy-β-uridine obtained in (a). While stirring the solution at room temperature, 0.5 ml of triethylamine was added and the resulting mixture was subjected to for about 4 hours. Thereafter, the mixture was treated in the same manner as in Example 1(b), except that the eluent for the column chromatography was a 10:1 mixture of chloroform and methanol. Thus, there was obtained 2.39 g (yield 80.5%) of crystalline 3-p-chloroacetylaminobenzoyl-5-fluoro-2'-deoxy-β-uridine having a melting point of 133°–137° C.

IR (KBr) cm$^{-1}$: $\nu_{C=O}$ 1735, 1700(sh), 1650

UV (ethanol) nm: $\lambda_{max}$ 205, 223, 301

Rf value: 0.61 (developing solvent: ethyl acetate:formic acid:water=65:5:5)

EXAMPLE 4

(a) At room temperature, 1.15 ml of triethylamine was dropped into a mixture of 3 g of 3',5'-di-O-chloroacetyl-5-fluoro-2'-deoxy-β-uridine, 1.7 g of p-dimethylaminobenzoyl chloride and 7.5 ml of anhydrous methylene chloride with stirring. The resulting mixture was subjected to at room temperature for about five hours and the reaction mixture was then washed with 20 ml of water, 20 ml of saturated aqueous solution of sodium bicarbonate and 20 ml of water in this order. It was dried over anhydrous sodium sulfate and the solvent was distilled off under reduced pressure, after which the residue was purified by silica gel column chromatography with chloroform as an eluent to obtain 3.8 g (yield 93%) of amorphous 3-p-dimethylaminobenzoyl-3',5'-di-O-chloroacetyl-5-fluoro-2'-deoxy-β-uridine.

IR (KBr) cm$^{-1}$: $\nu_{C=O}$ 1725, 1680, 1655

(b) In 10 ml of tetrahydrofuran was dissolved 3.8 g of the 3-p-dimethylaminobenzoyl-3',5'-di-O-chloroacetyl-5-fluoro-2'-deoxy-β-uridine obtained in (a), to which 10 ml of methanol was added. While stirring the solution at room temperature, 0.5 ml of triethylamine was added thereto and the reaction was effected for about one hour. Then the reaction mixture was concentrated under reduced pressure and the residue was purified by silica gel column chromatograhy (eluent: a 20:1 mixture of chloroform and methanol). The eluate was concentrated under reduced pressure and a small quantity of ethyl acetate was added to the concentrate. Thus, there was obtained 2.5 g (yield 92%) of crystalline 3-p-dimethyl-aminobenzoyl-5-fluoro-2'-deoxy-β-uridine having a melting point of 152°–154° C.

IR (KBr) cm$^{-1}$: $\nu_{C=O}$ 1720, 1695(sh), 1680, 1655

UV (ethanol) nm: $\lambda_{max}$ 204, 250, 274, 350

Rf value: 0.64 (developing solvent: ethyl acetate:formic acid:water=65:5:5)

EXAMPLE 5

The compounds listed in Table 6 were obtained in yields ranging from about 85% to 100% by carrying out the condensation reaction in the same manner as in Example 1(a).

TABLE 6

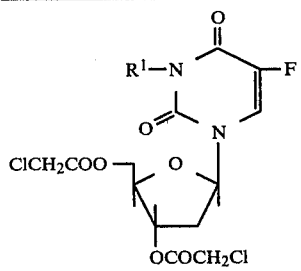

| $R^1$ | IR (film) cm$^{-1}$ $\nu_{C=O}$ | $R^1$ | IR (film) cm$^{-1}$ $\nu_{C=O}$ |
|---|---|---|---|
| 3,5-(CH$_3$O)$_2$C$_6$H$_3$—CO— | 1745, 1705, 1655 | CH$_3$CH=CHCO— | 1750, 1730 (sh), 1700, 1650 |
| | | CH$_3$(CH$_2$)$_6$CO— | 1740, 1705, 1660 |

TABLE 6-continued

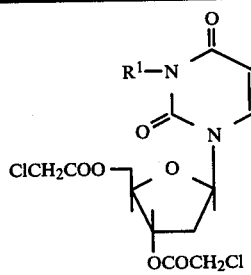

EXAMPLE 6

The compounds listed in Table 7 were obtained in yields ranging from 85% to 90% by repeating the procedures of Example 1(a) and (b).

| $R^1$ | IR (film) cm$^{-1}$ $\nu$C=O | $R^1$ | IR (film) cm$^{-1}$ $\nu$C=O |
|---|---|---|---|
| CH$_3$O—⌬—CO— | 1745, 1705, 1660 | Cl—⌬—CO— | 1765, 1760, 1660 |
| (2-OCH$_3$)C$_6$H$_4$—CO— | 1740, 1700, 1660 | C$_6$H$_5$—CH=CHCO— | 1740, 1705, 1660 |
| 2,3,4-(CH$_3$O)$_3$C$_6$H$_2$—CO— | 1745, 1710, 1670 | (2-OCH$_3$)C$_6$H$_4$—CH=CHCO— | 1740, 1700, 1660 |
| ClCH$_2$CONH—(3-OCH$_3$)C$_6$H$_3$—CO— | 1730, 1700 (sh), 1660 | 2-furyl—CO— | 1750, 1710, 1665 |
| 3,4,5-(CH$_3$O)$_3$C$_6$H$_2$—CO— | 1745, 1710, 1665 | 2-furyl—CH=CHCO— | 1730, 1690, 1665 |
| 2,6-(OCH$_3$)$_2$C$_6$H$_3$—CO— | 1740, 1710, 1665 | 3-pyridyl—CO— | 1750, 1710, 1665 |
| | | 3-(2,6-dichlorophenyl)-5-methylisoxazol-4-yl—CO— | 1750, 1710, 1670 |

TABLE 7
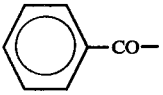
| R¹ | | Melting point (°C.) | IR (KBr or film) cm⁻¹ $\nu_{C=O}$ | UV (ethanol) nm $\lambda_{max}$ |
|---|---|---|---|---|
| 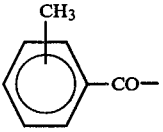 | | 147–148 | 1750, 1715, 1670 | 253, 282 (sh) |
| 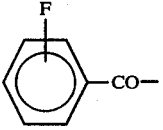 | ortho<br>meta<br>para | Amorphous<br>158<br>171–176 | 1735, 1695, 1645<br>1750, 1700, 1650<br>1730, 1700, 1630 | 208, 255, 285 (sh)<br>209, 257, 285 (sh)<br>206, 264 |
| 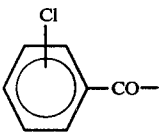 | ortho<br>meta | 129<br>149 | 1745, 1700, 1650<br>1755, 1705, 1650 | 205, 250, 285 (sh)<br>205, 251, 284 (sh) |
| 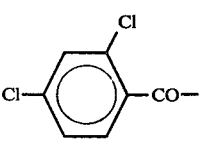 | ortho<br>meta | 115<br>153–155 | 1740, 1700, 1650<br>1750, 1700, 1650 | 255, 286 (sh)<br>209, 254, 284 (sh) |
| 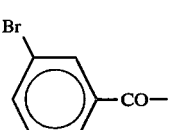 | | Amorphous | 1742, 1700, 1650 | 264, 210 |
| 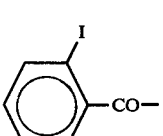 | | 141–142 | 1750, 1710, 1640 | 213, 255, 285 (sh) |
| 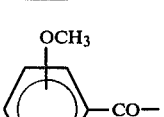 | | Amorphous | 1745, 1705, 1650 | 209, 231 (sh), 260, 270 (sh) |
| 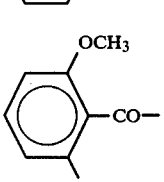 | ortho<br>para | Amorphous<br>119–120 | 1735, 1700, 1660<br>1735, 1690, 1650, 1620 | 211, 257, 321<br>203, 220, 286 |
|  | | 159–161 | 1730, 1680 (sh), 1650 | 212, 278, 329 (sh) |

TABLE 7-continued
| R[1] | Melting point (°C.) | IR (KBr or film) cm$^{-1}$ $\nu_{C=O}$ | UV (ethanol) nm $\lambda_{max}$ |
|---|---|---|---|
| 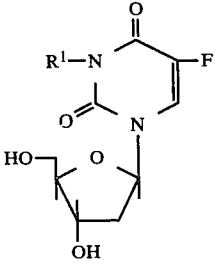 3,5-dimethoxybenzoyl | 159–160 | 1750, 1700, 1635 | 274, 335 |
| 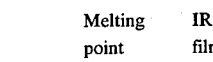 2,3,4-trimethoxybenzoyl | Amorphous | 1740, 1710, 1695, 1665 | 204, 215 (sh), 234 (sh), 284 |
| 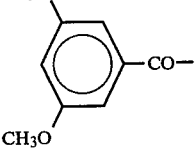 3,4,5-trimethoxybenzoyl | 170 | 1765, 1740, 1705, 1650 | 287 |
|  4-octyloxybenzoyl | 126–128 | 1740, 1700, 1650 (sh), 1630 | 204, 221, 289 |
| 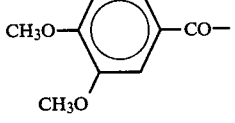 4-hydroxybenzoyl | 162–164 | 1735, 1695, 1635 | 204, 222, 291 (sh) |
| 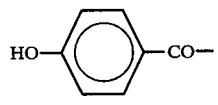 3,5-dihydroxybenzoyl | Oily | 1740, 1700, 1660 | 215, 271 |
| 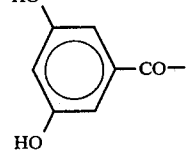 4-cyanobenzoyl | 145–146 | 1740, 1705, 1650 | 209, 263 |
| 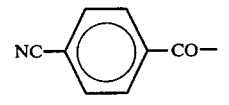 4-acetoxybenzoyl | 111–113 | 1745, 1700, 1650 | 260 |

TABLE 7-continued
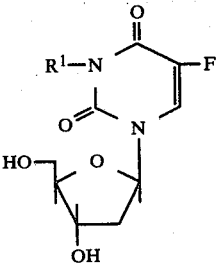
| R¹ | | Melting point (°C.) | IR (KBr or film) cm⁻¹ $\nu_{C=O}$ | UV (ethanol) nm $\lambda_{max}$ |
|---|---|---|---|---|
|  | | Amorphous | 1750, 1700, 1665 | 205, 241, 262 (sh), 325 (sh) |
| 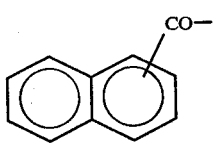 | α<br>β | Amorphous<br>Amorphous | 1720, 1685, 1640<br>1742, 1703, 1655 | 211, 250, 280, 330<br>208, 244 (sh), 253, 286, 297 (sh) |
| 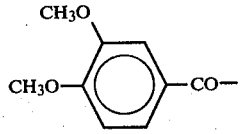 | | 165–167 | 1760, 1710, 1660 | 207, 233, 282, 315 |
| 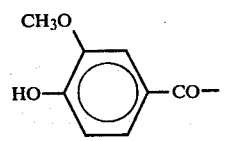 | | Amorphous | 1740, 1710, 1650 | 207, 220, 265, 310 |
| 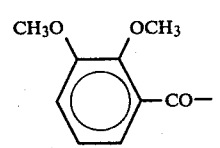 | | Oily | 1735, 1700, 1650 | 214, 266, 329 |
| 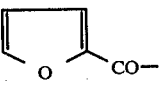 | | 160 | 1735, 1700, 1665 | 278 |
| 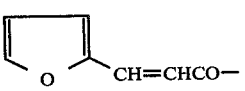 | | 138 | 1725, 1690, 1650 | 270 (sh), 333 |
| 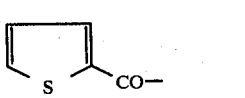 | | 145–146 | 1730, 1700, 1670 | 267 |
|  | | Amorphous | 1725, 1700, 1655 | 275 |
| 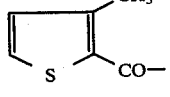 | | 155 | 1750, 1710, 1660 | 207, 223, 231 (sh), 300 |

TABLE 7-continued
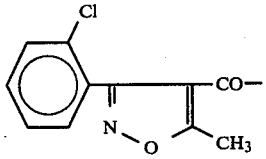
| R¹ | Melting point (°C.) | IR (KBr or film) cm⁻¹ $\nu_{C=O}$ | UV (ethanol) nm $\lambda_{max}$ |
|---|---|---|---|
| 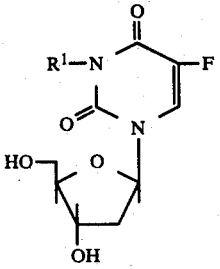 | Oily | 1740, 1705, 1660 | 204, 205, 288 (sh) |
| 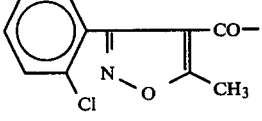 | Oily | 1750, 1710, 1660 | 206, 249, 273 (sh), 283 (sh) |
| 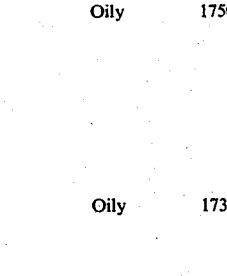 | Oily | 1730, 1700, 1650 | 211, 281 |
| 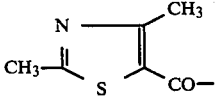 | Amorphous | 1750, 1710, 1650 | |
| $CH_3(CH_2)_6CO-$ | 145–146 | 1780, 1700 (sh), 1650 | |
| $CH_3(CH_2)_7CO-$ | 76–77 | 1780, 1705, 1635 | 204, 222, 290 |
| $CH_3(CH_2)_{14}CO-$ | 95–98 | 1780, 1710, 1640 | 207, 273 |
| $CH_3(CH_2)_{16}CO-$ | 103–105 | 1775, 1700, 1630 | 206, 273 |
| 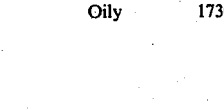 | 163–164 | 1740, 1700, 1660 | 205, 215, 298 |
| 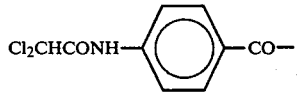 | 181–182 | 1750, 1707, 1658 | 203, 220 (sh), 294 |
|  | 129 | 1730, 1700, 1640 | 205, 222 (sh), 300 |
| 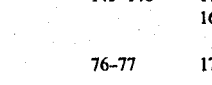 | 137–138 | 1740, 1705, 1635 | 205, 218 (sh), 289 |

TABLE 7-continued

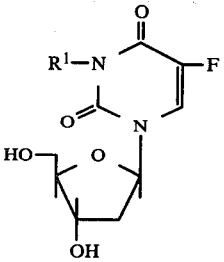

| R¹ | Melting point (°C.) | IR (KBr or film) cm⁻¹ $\nu_{C=O}$ | UV (ethanol) nm $\lambda_{max}$ |
|---|---|---|---|
|  | 174–175 | 1730, 1705, 1675 | 206, 287 |
|  | 166–167 | 1740, 1710, 1670 | 206, 291 |
| 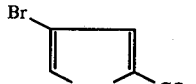 | 144–147 | 1720, 1690, 1640 | 208, 281 |
| 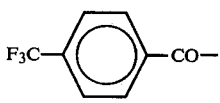 | 101–104 | 1760, 1710, 1655 | 204, 243, 280 (sh) |
| 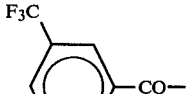 | 98–102 | 1760, 1715, 1660 | 205, 247, 278 (sh) |
|  | 133–135 | 1735, 1695, 1630 | 206, 236, 279, 321 |
| 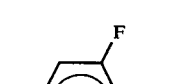 | 107–110 | 1760, 1715, 1670 | 281 (sh), 251, 205.5 |
| 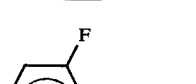 | 123 | 1765, 1710, 1645 | 276, 247, 204.5 |

EXAMPLE 7

In 10 ml of chloroform was suspended 2.46 g (0.01 mole) of 5-fluoro-2'-deoxy-β-uridine, to which 5.5 ml (0.04 mole) of triethylamine and 2.8 ml (0.022 mole) of trimethylsilyl chloride were added in this order. The mixture was subjected to reaction under reflux for one hour, after which 2.2 g (0.012 mole) of 3,4-methylenedioxybenzoyl chloride was added thereto and the mixture was refluxed for an additional 30 minutes. While cooling the reaction mixture with ice, 10 ml of 1N methanolic solution of hydrogen chloride was added. The mixture was stirred at that temperature for 30 minutes and then neutralized with triethylamine. The reaction mixture was concentrated to dryness, and the residue was dissolved in ethyl acetate, after which the resulting solution was washed with dilute hydrochloric acid, saturated aqueous solution of sodium bicarbonate and water in this order, dried over anhydrous magnesium sulfate, and subjected to distillation under reduced pressure to remove the solvent. The residue was mixed with 40 ml of a chloroform-methanol mixture (20:1) and the insoluble matter was collected by filtration to obtain 3.7 g (yield 94%) of crystalline 3-(3,4-methylenedioxybenzoyl)-5-fluoro-2'-deoxy-β-uridine having a melting point of 133°–135° C.

Rf value: 0.56 (developing solvent: chloroform:acetone:methanol = 5:5:1)

EXAMPLE 8

In 10 ml of chloroform was suspended 2.46 g (0.01 mole) of 5-fluoro-2'-deoxy-β-uridine, to which 5.5 ml (0.04 mole) of triethylamine and 3.1 g (0.022 mole) of 2-chloro-4-methyl-1,3,2-dioxaphospholane were added in this order. The mixture was subjected to reaction at room temperature for 3 hours with stirring. Then, 2.2 g (0.012 mole) of 3,4-methylenedioxybenzoyl chloride was added thereto and the resulting mixture was subjected to at room temperature for 4 hours with stirring. After the reaction, 10 ml of 1N methanolic solution of hydrogen chloride was added to the reaction mixture.

Thereafter, it was treated in the same manner as in Example 6. Thus, there was obtained 3.5 g (yield 89%) of crystalline 3-(3,4-methylenedioxybenzoyl)-5-fluoro-2'-deoxy-β-uridine having a melting point of 133°–135° C.

EXAMPLE 9

At room temperature, 0.93 ml of triethylamine was dropped into a mixture of 2 g of 3',5'-di-O-acetyl-5-fluoro-2'-deoxy-β-uridine, 1.3 g of 3,4-methylenedioxybenzoyl chloride and 5 ml of anhydrous methylene chloride with stirring. After completion of the dropping, the resulting mixture was subjected to at room temperature for 5 hours. Then it was washed with 15 ml of water, 15 ml of saturated aqueous solution of sodium bicarbonate and 15 ml of water in this order, and the organic layer was dried over anhydrous sodium sulfate, and subjected to distillation under reduced pressure to remove the solvent. The residue was purified by silica gel column chromatography (eluent:chloroform) to obtain 2.7 g (yield 94.5%) of amorphous 3-(3,4-methylenedioxybenzoyl)-3',5'-di-O-acetyl-5-fluoro-2'-deoxy-β-uridine.

IR (KBr) cm$^{-1}$: $\nu_{C=O}$ 1745, 1710, 1670

UV (ethanol) nm: $\lambda_{max}$ 206, 236, 279, 321

Rf value: 0.47 (developing solvent: n-hexane:benzene:ethyl acetate = 1:1:2)

EXAMPLE 10

At room temperature, 0.41 ml of triethylamine was dropped into a mixture of 1.04 g of 2',3',5'-tri-O-chloroacetyl-5-fluoro-β-uridine, 0.49 g of p-methylbenzoyl chloride and 5 ml of anhydrous methylene chloride with stirring. After completion of the dropping, the resulting mixture was subjected to reaction at room temperature for about 5 hours. The reaction mixture was washed with 10 ml of water, 10 ml of saturated aqueous solution of sodium bicarbonate and 10 ml of water in this order, and the organic layer was dried over anhydrous sodium sulfate, and subjected to distillation under reduced pressure to remove the solvent. The residue was dissolved in 5 ml of tetrahydrofuran, to which 5 ml of methanol was added, and 0.25 ml of triethylamine was further added at room temperature with stirring. The mixture was subjected to reaction for about 10 hours and then concentrated under reduced pressure. The concentrate was purified by silica gel column chromatography (eluent:chloroform:methanol = 20:1), the eluate was concentrated under reduced pressure, and a small quantity of methylene chloride was added to the concentrate. Thus, there was obtained 0.65 g (yield 82%) of crystalline 3-p-methylbenzoyl-5-fluoro-β-uridine having a melting point of 167°–168° C.

IR (KBr) cm$^{-1}$: $\nu_{C=O}$ 1740, 1700, 1655

UV (ethanol) nm: $\lambda_{max}$ 205, 264

Rf value: 0.63 (developing solvent: ethyl acetate:formic acid:water = 65:5:5)

EXAMPLE 11

The compounds listed in Table 8 were obtained in yields ranging from about 80% to 100% by carrying out the reaction in the same manner as in Example 10.

TABLE 8

| $R^1$ | Melting point (°C.) | IR (KBr) (cm$^{-1}$) $\nu_{C=O}$ | UV (ethanol) (nm) $\lambda_{max}$ |
|---|---|---|---|
| (CH$_3$)$_2$N—⟨◯⟩—CO— | 170–172 | 1725, 1655, 1590 | 203, 250, 274, 350 |
| CF$_3$CONH—⟨◯⟩—CO— | 220 | 1740, 1710, 1660 | 205, 286 |

TABLE 8-continued

![structure of 5-fluoro-2'-deoxy-uridine derivative with R1-N]

| R¹ | Melting point (°C.) | IR (KBr) (cm⁻¹) $\nu_{C=O}$ | UV (ethanol) (nm) $\lambda_{max}$ |
|---|---|---|---|
| 3,4,5-trimethoxybenzoyl (CH₃O)₃C₆H₂—CO— | 180 | 1755, 1702, 1650 | 215, 284 |
| 4-fluorobenzoyl F—C₆H₄—CO— | 144–150 | 1740, 1700, 1650 | 206, 254, 270 (sh) |
| 3,4-methylenedioxybenzoyl | 80–85 | 1740, 1705, 1655 | 204, 232, 277, 318 |

Typical examples of the preparation containing the compounds of this invention are as follows:

PREPARATION EXAMPLE 1

Into a vial was sealed 200 mg of sterilized 3-(3,4-methylenedioxybenzoyl)-5-fluoro-2'-deoxy-β-uridine. Prior to use, it was dissolved in 10 ml of 5% aqueous glucose solution containing 5 ml of sterile propylene glycol and further diluted with 500 ml of 5% aqueous glucose solution. The dilute solution was used for intravenous drip.

PREPARATION EXAMPLE 2

One handred milligrams of sterilized 3-(3,4-methylenedioxybenzoyl)-5-fluoro-2'-deoxy-β-uridine, 100 mg of potato starch, 70 mg of lactose, 10 ml of crystalline cellulose and 0.5 mg of magnesium stearate were mixed together and formed into a capsule.

What is claimed is:

1. A 5-fluoro(2'-deoxy-β-uridine)derivative of the formula

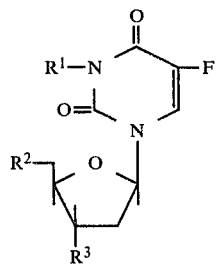

wherein R¹ is aroyl, $C_{1-18}$alkanoyl, heterocyclic carbonyl the heterocyclic ring of which contains 1–4 hetero atoms or $C_{3-5}$alkenoyl, said R¹ substituents optionally being substituted with at least one substituent selected from the group consisting of halogen, hydroxyl, nitro, cyano, amino, carboxyl, $C_{1-12}$acyl, $C_{1-12}$acyloxy, $C_{1-5}$alkylamino, di-$C_{1-5}$alkylamino, $C_{1-12}$acylamino, $C_{1-5}$alkyl, $C_{1-10}$alkoxy, $C_{1-5}$alkoxycarbonyl, aryl, heterocyclic group wherein the heterocyclic ring contains from one to four hetero atoms and halogen substituted derivatives of said $C_{1-12}$acyl, $C_{1-12}$acyloxy, $C_{1-5}$alkylamino, di-$C_{1-5}$alkylamino, $C_{1-12}$acylamino, $C_{1-5}$alkyl, $C_{1-10}$alkoxy, $C_{1-5}$alkoxycarbonyl, aryl and heterocyclic groups; and R² and R³, which may be identical or different represent protected or unprotected hydroxyl.

2. The 5-fluoro-(2'-deoxy-β-uridine)derivative of claim 1, wherein said aroyl substituent is benzoyl or 3,4-methylenedioxybenzoyl.

3. The 5-fluoro-(2'-deoxy-β-uridine)derivative of claim 1, wherein said heterocyclic carbonyl is furoyl, theonyl, thiazolylcarbonyl, oxazolylcarbonyl, isoxazolylcarbonyl or nicotinoyl.

4. The 5-fluoro-(2'-deoxy-β-uridine)derivative of claim 1, wherein said protecting group for said hydroxyl substituent at R² and R³ is a member selected from the group consisting of $C_{1-10}$alkanoyl, $C_{1-10}$alkoxycarbonyl, $C_{1-12}$acyloxy-$C_{1-12}$acyl, p-chlorobenzoyl, p-methylbenzoyl, p-nitrobenzoyl, m,p-dinitrobenzoyl and mono-, di- or trihalogeno-$C_{1-10}$alkanoyl.

5. The 5-fluoro-(β-uridine or 2'-deoxy-β-uridine)-derivative according to claim 2, wherein R¹ is benzoyl substituted by fluorine, chlorine, bromine or iodine or fluorine, chlorine, bromine or iodine substituted acetylamino, or 3,4-methylenedioxybenzoyl.

6. The 5-fluoro-(2'-deoxy-β-uridine) derivative according to claim 5, wherein $R^1$ is benzoyl substituted by fluorine or chloroacetylamino, or 3,4-methylenedioxybenzoyl.

7. The 5-fluoro-2'-deoxy-β-uridine derivative of claim 1, 2, 3, 5 or 6, wherein $R^2$ and $R^3$ are both hydroxyl.

8. 3-(3,4-Methylenedioxybenzoyl)-5-fluoro-2'-deoxy-β-uridine.

9. 3-(3,4-Methylenedioxybenzoyl)-3',5'-di-O-acetyl-5-fluoro-2'-deoxy-β-uridine.

10. 3-p-Monochloroacetylaminobenzoyl-5-fluoro-2'-deoxy-β-uridine.

11. 3-p-Fluorobenzoyl-5-fluoro-2'-deoxy-β-uridine.

12. A pharmaceutical composition having carcinostatic activity on tumors transplanted into animals, which comprises:

a carcinostatically effective amount of the compound in claim 1, in combination with a pharmaceutically acceptable inert excipient or diluent.

* * * * *